United States Patent
Ludin et al.

(10) Patent No.: US 9,808,607 B2
(45) Date of Patent: Nov. 7, 2017

(54) SYSTEM AND METHOD FOR DETERMINING POSITION AND PRESSURE OF AN IMPLANTABLE SHUNT

(71) Applicant: DePuy Synthes Products, LLC, Raynham, MA (US)

(72) Inventors: Lev Ludin, Newton, MA (US); Michael DeFusco, North Attleboro, MA (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 165 days.

(21) Appl. No.: 14/847,766

(22) Filed: Sep. 8, 2015

(65) Prior Publication Data

US 2015/0374961 A1 Dec. 31, 2015

Related U.S. Application Data

(62) Division of application No. 13/796,164, filed on Mar. 12, 2013, now Pat. No. 9,126,009.

(51) Int. Cl.
  *A61M 27/00* (2006.01)
(52) U.S. Cl.
  CPC ........ *A61M 27/002* (2013.01); *A61M 27/006* (2013.01); *A61M 2202/0464* (2013.01);
  (Continued)
(58) Field of Classification Search
  CPC .. A61M 2202/0464; A61M 2205/3331; A61M 2205/3334; A61M 2205/3344;
  (Continued)

(56) References Cited

U.S. PATENT DOCUMENTS

| 2,813,958 A | 11/1957 | MacDonald |
| 4,041,954 A | 8/1977 | Ohara |

(Continued)

FOREIGN PATENT DOCUMENTS

| EP | 1669042 A2 | 6/2006 |
| WO | 2009/113037 A1 | 9/2009 |

OTHER PUBLICATIONS

European Search Report dated Sep. 26, 2014, which issued during prosecution of European Application No. 14158711.3, which corresponds to the present application.

*Primary Examiner* — Adam Marcetich
(74) *Attorney, Agent, or Firm* — Troutman Sanders LLP (57) ABSTRACT

In one aspect, an implantable shunt system is disclosed that, in one example implementation, includes a resilient member and a connected fluid regulating device. The fluid regulating device selectively permits fluid flow through an opening valve of an implantable shunt according to an adjustable opening pressure. The opening pressure is proportional to an amount of tension on the resilient member. One or more tension sensors that are connected to the resilient member measure an amount of tension on the resilient member. The tension sensors generate tension data that corresponds to the measured amount of tension. The system further includes a communication unit with a transmitting unit that transmits the measured data over a communication link. The system also includes a reading unit that receives the transmitted tension data over the communication link. The reading unit includes a connector that electrically connects the reading unit to the transmission unit.

11 Claims, 8 Drawing Sheets

(52) U.S. Cl.
CPC ............... *A61M 2205/3331* (2013.01); *A61M 2205/3334* (2013.01); *A61M 2205/3344* (2013.01); *A61M 2205/3507* (2013.01); *A61M 2205/3523* (2013.01); *A61M 2210/0687* (2013.01); *A61M 2210/0693* (2013.01)

(58) Field of Classification Search
CPC .. A61M 2205/3507; A61M 2205/3523; A61M 2210/0687; A61M 2210/0693; A61M 27/002; A61M 27/006; A61M 2205/35; A61M 2205/3538; A61B 5/0002; A61B 5/0015; A61B 5/0026; A61B 5/0031
See application file for complete search history.

(56) References Cited

U.S. PATENT DOCUMENTS

| | | | |
|---|---|---|---|
| 4,593,703 A | 6/1986 | Cosman | |
| 4,619,653 A | 10/1986 | Fischell | |
| 5,643,195 A | 7/1997 | Drevet et al. | |
| 6,070,102 A | 5/2000 | Hartlaub et al. | |
| 6,685,638 B1 | 2/2004 | Taylor et al. | |
| 6,979,351 B2 | 12/2005 | Forsell et al. | |
| 7,311,690 B2 | 12/2007 | Burnett | |
| 7,335,179 B2 | 2/2008 | Burnett | |
| 7,621,878 B2 | 11/2009 | Ericson et al. | |
| 7,842,004 B2 | 11/2010 | Kassem | |
| 8,123,714 B2 | 2/2012 | Ludin et al. | |
| 8,177,737 B2 | 5/2012 | Negre et al. | |
| 8,282,566 B2 | 10/2012 | Mauge et al. | |
| 2002/0052563 A1 | 5/2002 | Penn et al. | |
| 2004/0267186 A1 | 12/2004 | Dextradeur et al. | |
| 2005/0061079 A1* | 3/2005 | Schulman | A61B 5/0031 73/715 |
| 2005/0096579 A1* | 5/2005 | Bertrand | A61M 27/006 604/9 |
| 2005/0159660 A1 | 7/2005 | Montegrande et al. | |
| 2006/0195043 A1* | 8/2006 | Rutherford | A61B 5/032 600/561 |
| 2006/0211912 A1 | 9/2006 | Dlugos et al. | |
| 2007/0004999 A1 | 1/2007 | Miethke | |
| 2007/0005000 A1 | 1/2007 | Ludin | |
| 2008/0097277 A1 | 4/2008 | Saunders | |
| 2008/0214983 A1 | 9/2008 | Mauge et al. | |
| 2009/0005701 A1 | 1/2009 | Dextradeur et al. | |
| 2009/0005720 A1 | 1/2009 | Ludin et al. | |
| 2009/0107233 A1 | 4/2009 | Kassem | |
| 2009/0112103 A1 | 4/2009 | Kassem | |
| 2009/0112147 A1 | 4/2009 | Kassem | |
| 2009/0112308 A1 | 4/2009 | Kassem | |
| 2009/0143696 A1 | 6/2009 | Najafi et al. | |
| 2009/0204019 A1 | 8/2009 | Ginggen et al. | |
| 2009/0270942 A1 | 10/2009 | Heruth et al. | |
| 2010/0022896 A1 | 1/2010 | Yadav et al. | |
| 2010/0030103 A1 | 2/2010 | Lutze et al. | |
| 2010/0076366 A1 | 3/2010 | Henderson et al. | |
| 2010/0193463 A1 | 8/2010 | O'Brien et al. | |
| 2010/0262036 A1 | 10/2010 | Najafi et al. | |
| 2010/0268151 A1 | 10/2010 | Mauge et al. | |
| 2010/0312164 A1 | 12/2010 | Forsell | |
| 2011/0040233 A1 | 2/2011 | Kassem | |
| 2011/0112460 A1 | 5/2011 | Murphy | |
| 2011/0224595 A1 | 9/2011 | Pedersen et al. | |
| 2011/0275976 A1 | 11/2011 | Negre et al. | |
| 2012/0232461 A1* | 9/2012 | Seaver | A61M 27/006 604/9 |
| 2012/0259265 A1 | 10/2012 | Salehi et al. | |
| 2012/0302938 A1 | 11/2012 | Browd et al. | |
| 2013/0197390 A1 | 8/2013 | Weinberg et al. | |

* cited by examiner

SYSTEM AND METHOD FOR DETERMINING POSITION AND PRESSURE OF AN IMPLANTABLE SHUNT

CROSS-REFERENCE TO RELATED APPLICATION

This application claims priority to and is a divisional of U.S. patent application Ser. No. 13/796,164, filed Mar. 12, 2013, the contents of which is hereby incorporated by reference herein in its entirety.

BACKGROUND

Implantable shunt systems are used in the medical field for directing body fluid from one region to another. To treat patients with hydrocephalus, fluid shunt systems can be used to remove and discharge excess cerebrospinal fluid ("CSF"). Draining the excess fluid relieves elevated intracranial pressure. Generally, valve mechanisms control or regulate the flow rate of fluid through the shunt system. The valve mechanisms may permit fluid flow only when fluid pressure reaches a certain threshold level. The fluid flow rate is proportional to the pressure at the valve mechanism and thus, for a pressure that is only slightly higher than the threshold or opening pressure, the flow rate is relatively low. As the fluid pressure increases, the flow rate through the shunt system increases. At pressures that are significantly higher than the threshold pressure, a maximum flow rate for the system is reached. Fluid flow normally continues until the intracranial pressure has been reduced to a level less than the threshold pressure.

The threshold or opening pressure that allows fluid flow through a shunt system often needs to be adjusted. A medical professional may initially select a relatively low opening pressure to trigger fluid flow. Over time, the initial opening pressure may require adjustment, for example in a situation where excess fluid flow creates an undesirable overdrainage condition, which may necessitate an increase in the opening pressure to produce a fluid flow rate that is balanced. Some valve systems allow a medical professional to non-invasively customize an implanted valve mechanism's opening pressure for a particular patient.

A Hakim valve is a commonly used differential pressure valve having selectable precise opening pressures. Current practice may require that an x-ray be taken to verify a new setting after each valve adjustment. Conventional approaches for determining valve position can have undesirable complications. As an example, when magnetic fields are used for verifying valve position, metallic equipment within a clinical environment may interfere with the accuracy of information obtained through the use of these magnetic forces, which can lead to inaccurate readings.

U.S. Pat. No. 6,685,638 describes an apparatus for acoustically monitoring the position of a Hakim shunt. In some circumstances, it may be difficult to accurately determine valve position using acoustics. For example, environmental factors such as the presence of ambient sound may in some cases effectively limit the signal-to-noise ratio of an acoustic reading. Also, it may be challenging to clearly identify acoustic position signals across all patients because the thickness of subcutaneous layers of tissue can vary from patient to patient.

It is with respect to these and other considerations that the various example implementations described below are presented.

SUMMARY

In one aspect, the present invention relates to an implantable shunt system. In one example implementation, the system includes a resilient member and a fluid regulating device that is connected to the resilient member. The fluid regulating device selectively permits fluid flow through an opening valve of an implantable shunt, according to an adjustable opening pressure. The opening pressure is proportional to an amount of tension on the resilient member. The system also includes one or more tension sensors that are connected to the resilient member and measure an amount of tension on the resilient member. The tension sensors generate tension data that corresponds to the measured amount of tension. The system further includes a communication unit including a transmitting unit. The transmitting unit transmits the tension data over a communication link.

In another aspect, the present invention relates to an implantable shunt that, in one example implementation, includes a resilient member and a fluid regulating device that is connected to the resilient member. The fluid regulating device includes a sealing member that is selectively engaged at a valve opening to permit fluid with a fluid pressure that is at or above an adjustable threshold opening pressure to flow through the valve opening. The threshold opening pressure is proportional to an amount of tension on the resilient member. The implantable shunt also includes tension sensors that are connected to the resilient member and are each located at a different respective position on the resilient member. The tension sensors measure an amount of tension on the resilient member and generate tension data that corresponds to the measured amount of tension. The implantable shunt further includes a communication unit that includes a transmitting unit. The transmitting unit transmits the tension data over a communication link.

In yet another aspect, the present invention relates to a method of determining pressure and position of an implantable shunt. In one example implementation, the method includes measuring an amount of tension on a resilient member of the implantable shunt, via one or more tension sensors that are connected to the resilient member. The tension sensors generate tension data that corresponds to the measured amount of tension. The method also includes transmitting, by a transmitting unit, the generated tension data over a communication link.

BRIEF DESCRIPTION OF THE DRAWINGS

Other aspects and features of example implementations of the present invention will become apparent to those of ordinary skill in the art, upon reviewing the following detailed description in conjunction with the accompanying figures.

DETAILED DESCRIPTION

Although example implementations of the present invention are explained in detail, it is to be understood that other implementations are contemplated. Accordingly, it is not intended that the present invention be limited in its scope to the details of construction and arrangement of components set forth in the following description or illustrated in the drawings. The present invention is capable of other implementations and of being practiced or carried out in various ways.

It must also be noted that, as used in the specification and the appended claims, the singular forms "a," "an" and "the" include plural referents unless the context clearly dictates otherwise.

In describing example implementations, terminology will be resorted to for the sake of clarity. It is intended that each term contemplates its broadest meaning as understood by those skilled in the art and includes all technical equivalents that operate in a similar manner to accomplish a similar purpose.

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more operations according to a method does not preclude the presence of additional operations or intervening operations between those expressly identified. Operations of a method may be performed in a different order than those described herein. Similarly, it is also to be understood that the mention of one or more components in a device or system does not preclude the presence of additional components or intervening components between those components expressly identified.

In the following detailed description, references are made to the accompanying drawings that form a part hereof and that show, by way of illustration, specific implementations or examples. In referring to the drawings, like numerals represent like elements throughout the several figures.

Figure 1A:
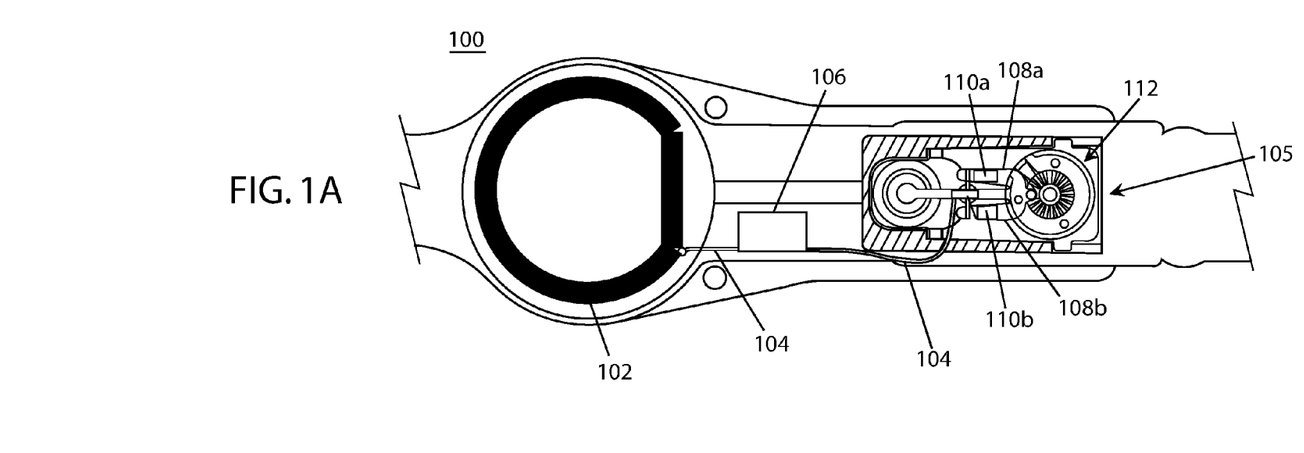
FIG. 1A is a top sectional view of an implantable shunt according to an example implementation of the present invention.
Figure 1B:
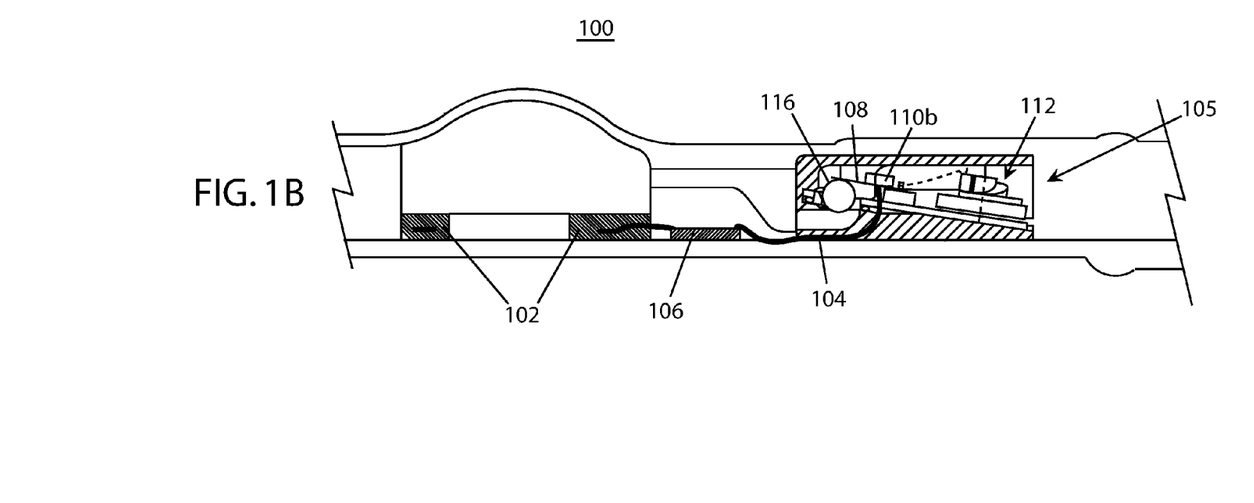
FIG. 1B is a side sectional view of the implantable shunt according to the example implementation shown in FIG. 1A.

FIGS. 1A and 1B provide a top sectional view and side sectional view of an implantable shunt 100 according to an example implementation of the present invention. The implantable shunt 100 includes a resilient member 108 with two sides 108a, 108b and a fluid regulating device 116 connected to the resilient member 108. The fluid regulating device 116 selectively permits fluid flow through the implantable shunt 100 according to an adjustable opening pressure that is proportional to an amount of tension on the resilient member 108. Two tension sensors 110a and 110b are connected to the two respective sides 108a, 108b of the resilient member 108. The tension sensors 110a, 110b measure an amount of tension on the resilient member 108 and generate tension data that corresponds to the measured amount of tension.

It should be appreciated that more or less than two tension sensors may be used without departing from the scope of the present invention disclosed herein. For example, a single tension sensor that is centrally placed on the resilient member 108 may alternatively be used. As further shown in FIG. 1D, a communication unit 132 is electrically connected by wires 104 to the tension sensors 110a, 110b. A wireless antenna 102 of the communication unit 133 (see FIGS. 1A and 1B) transmits the tension data over a wireless communication link. The communication unit 132 also receives an activation command signal from a reading unit 134 over the wireless communication link 133, via the wireless antenna 102.

Figure 1C:
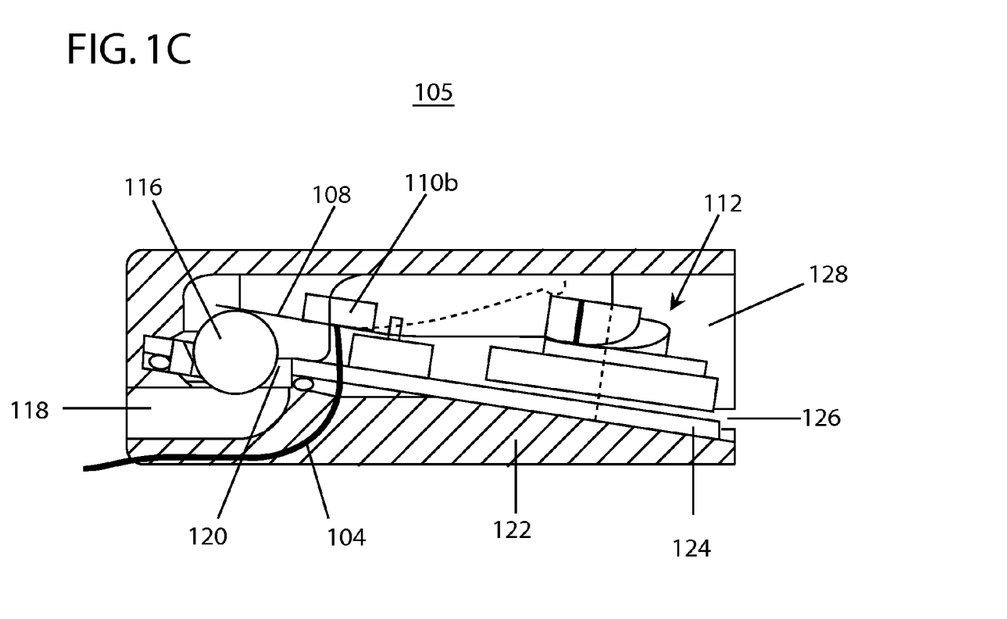
FIG. 1C is an enlarged, side sectional view of a portion of the implantable shunt according to the example implementation shown in FIGS. 1A and 1B.
Figure 1D:
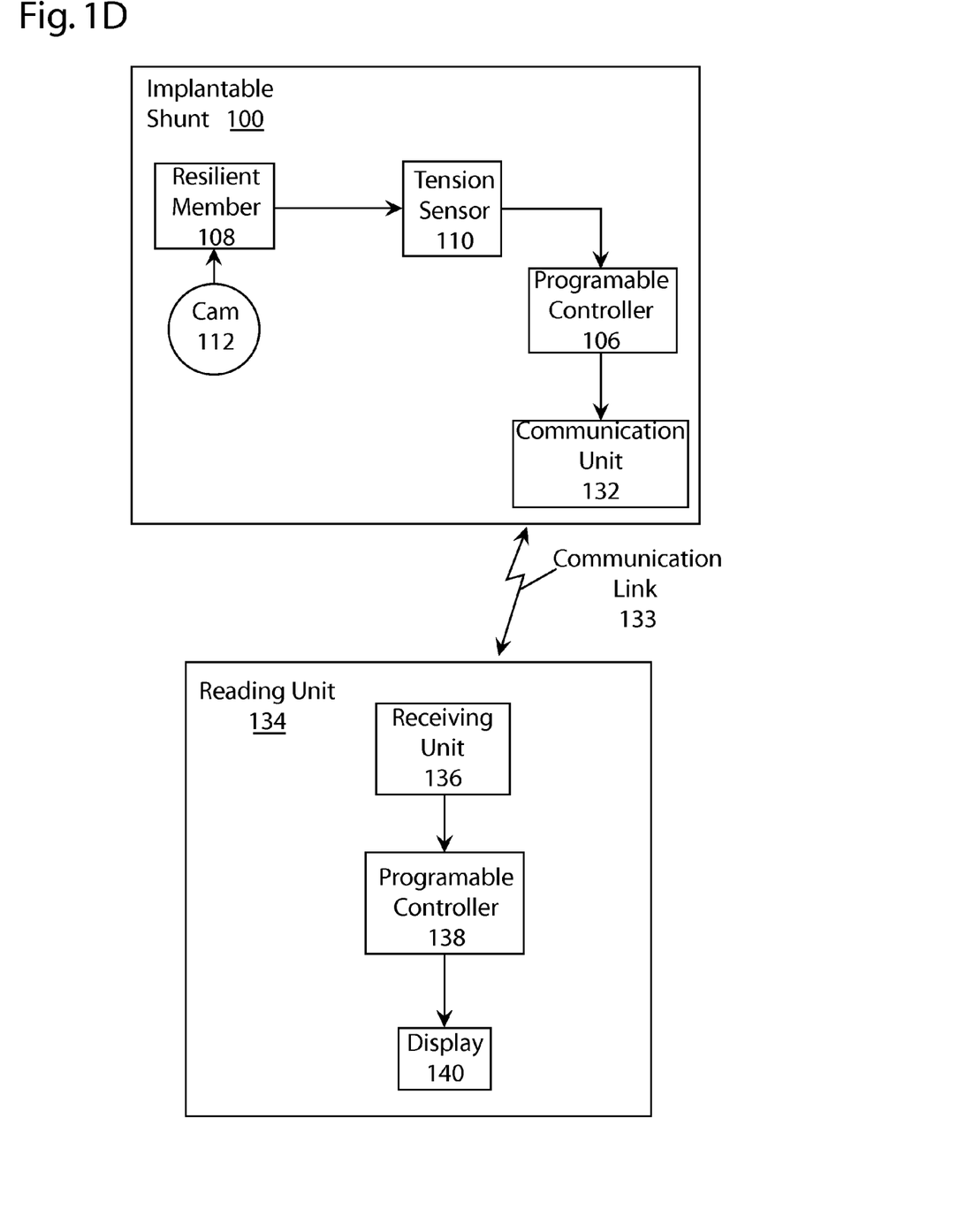
FIG. 1D is a block diagram illustrating an implantable shunt system including the implantable shunt according to the example implementation of the present invention shown in FIGS. 1A-C.

A programmable controller 106 that is electrically connected to the communication unit 132 causes the tension sensors 110a, 110b to measure the tension on the resilient member 108 in response to receiving the activation command signal via the wireless antenna 102. The programmable controller 106 also causes the communication unit 132 to transmit the tension data to the reading unit 134 over the wireless communication link 133 in response to receiving the activation command signal. The reading unit 134 has a receiving unit 136 with a wireless transmitter and receiver that transmits the activation command signal and receives the transmitted tension data from the communication unit 132, respectively. The reading unit 134 has a programmable controller 138 that is electronically connected to the receiving unit 136 and determines a pressure and/or position associated with the implanted shunt 100, based on the received tension data.

The programmable controller 106 determines the opening pressure of the fluid regulating device 116 based on the received tension data. A position of a cam 112 can also be determined by the programmable controller 106 based on the received tension data. The cam 112 is connected to the resilient member 108, and the tension on the resilient member 108 is proportional to the position of the cam 112. As shown in FIG. 1D, the reading unit 134 also includes a display 140 that is connected to the programmable controller 106 and displays one or more visual representations associated with the received tension data.

The example implementation of the implantable shunt 100 and reading unit 134 shown in FIGS. 1A-1D will now be described in further detail. FIG. 1C provides an enlarged view of a portion of the implantable shunt 100 and, more particularly, a shunt valve 105 of the implantable shunt 100. The shunt 100 can be surgically implanted under the scalp of a patient and configured for hydrocephalus, and may be configured with components of a Hakim programmable shunt. The shunt valve 105 includes a valve body 122 that defines a chamber 128 with an inlet opening 118 and an outlet opening 126. When fluid pressure at the inlet opening 118 exceeds a predetermined threshold pressure, fluid begins to flow through the shunt valve 105. A support plate 124 within the valve body 122 has an aperture with a valve seat 120. The fluid regulating device 116 is a ball that selectively engages with the valve seat 120. As shown, the resilient member 108 is a spring that biases the ball 116 to the valve seat 120 to selectively allow or prevent fluid flow.

The biasing force of the spring 108 is adjustable by means of the cam 112. The cam 112 includes a plurality of steps of varying vertical position with respect to the support plate 124. Each step of the cam 112 provides a discrete pressure on the ball 116 via the spring 108. Thus, changing position of the cam 112 changes the tension on the spring 108. The biasing force provided by the spring 108 dictates the threshold pressure that must be overcome in order to disengage the ball 116 from the valve seat 120 to thereby allow fluid flow into the chamber 128.

Those skilled in the art will recognize that after a shunt valve is surgically implanted under the scalp of a patient, the threshold pressure can be adjusted using external programming devices, which can adjust the opening pressure at which fluid begins to flow through the shunt valve. Electromagnets can be disposed about a central axis and sequentially energized to apply a pulsed magnetic field to a stepper motor (not illustrated) of the cam 112, to cause a rotor to rotate. This causes the cam 112 to rotate and therefore adjust the pressure applied to the ball 116 by one end of a spring 108.

Referring again specifically to the example implementation shown in FIGS. 1A-1D, the tension sensors 110a, 110b are configured as strain gauges that are attached to the surface of a beam of the spring 108, and may include resistive, capacitive, and/or semiconductor type sensors. Using two strain gauges instead of a single strain gauge may minimize errors in the tension measurements caused by temperature fluctuations, for example. The programmable controller 106 is an application specific integrated circuit (ASIC) that can include one or more processors, a memory connected to the processors, and one or more storage devices for storing non-transitory data and instructions that, when executed by the one or more processors, cause the ASIC 106 to perform specific functions described herein with respect to FIGS. 1A-1D and/or operations of the method 500 described below with respect to FIG. 5. The ASIC 106 can include a signal conditioner to convert analog signals from the strain gauges 110a, 110b, corresponding to tension measurements, into tension data in digital form. The communication unit 132 can include an RF transmitter and RF receiver with a wireless antenna for transmitting the tension data to the reading unit 134 and receiving the activation command signal from the reading unit 134.

The receiving unit 136 can include an RF transmitter and RF receiver with a wireless antenna for receiving the tension data and transmitting the activation command signal. A programmable controller 138 of the reading unit is electrically connected to the receiving unit 136 and may include one or more processors, a memory connected to the one or more processors, and one or more storage devices for storing non-transitory data and instructions that, when executed by the one or more processors, cause the programmable controller 106 to perform specific functions described herein with respect to FIGS. 1A-1D and/or operations of the method 500 described below with respect to FIG. 5. The reading unit 134 also includes a display 140 that is electrically connected to the programmable controller 106, that displays one or more visual representations associated with the received tension data, such as plots, graphs, tables, and/or numerical representations of position and/or pressure of the implantable shunt 100 as indicated by the tension data. Power to the ASIC 106 of the shunt 100 can be provided remotely by passive telemetry using the RF transmitter of the receiving unit 136 and RF receiver of the communication unit 132, via the wireless antenna. The electronic components of the shunt 100, including the ASIC 106 and strain gauges 110a, 110b, can be kept in a dormant, sleep mode until the power is provided.

Figure 2A:
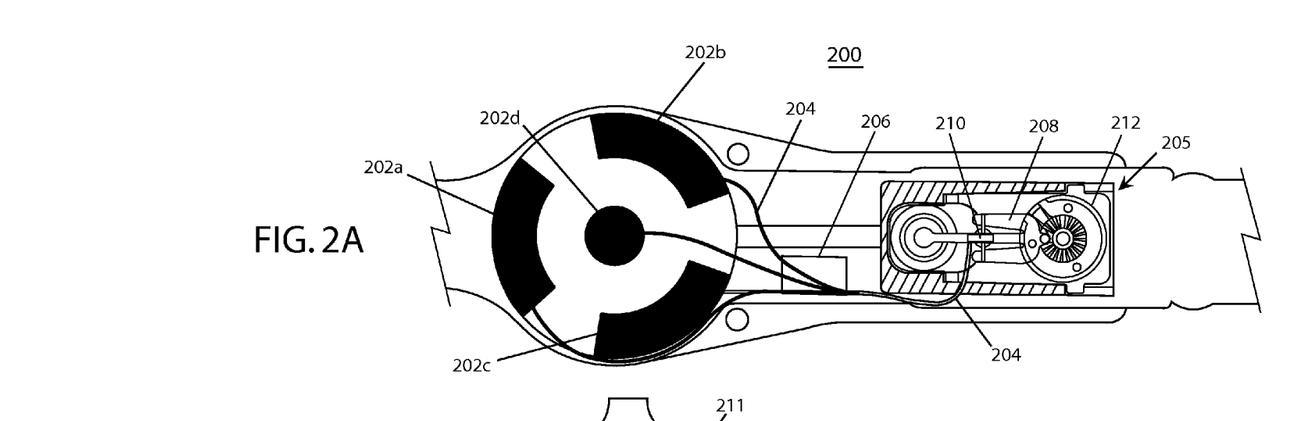
FIG. 2A is a top sectional view of an implantable shunt according to another example implementation of the present invention.
Figure 2B:
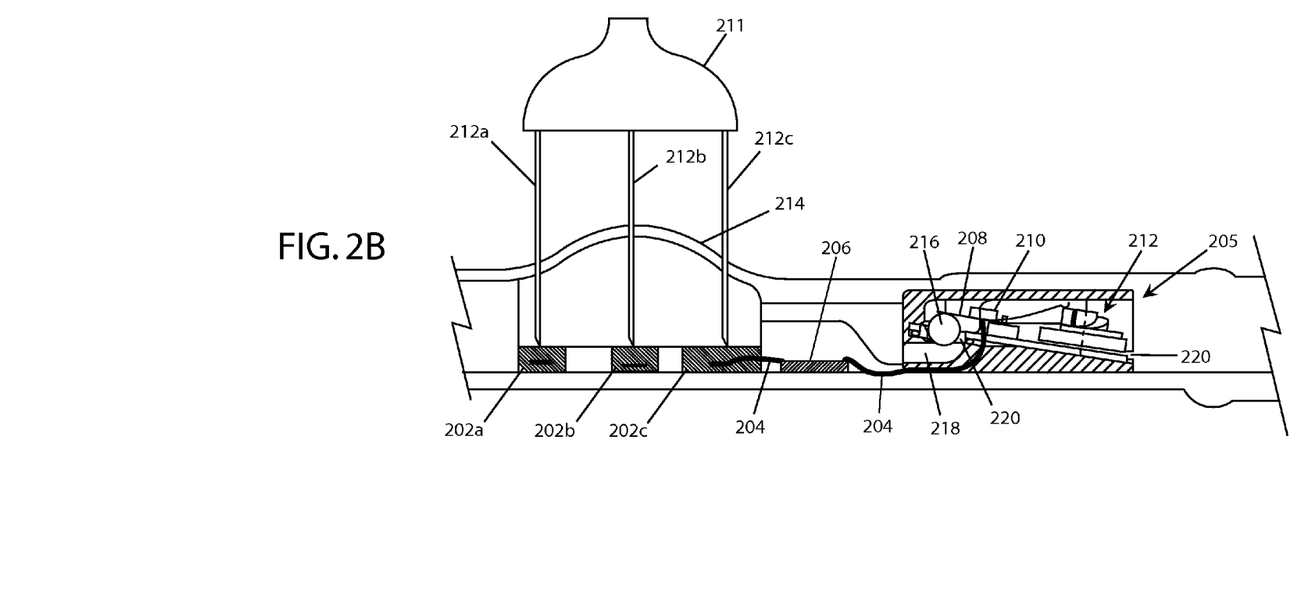
FIG. 2B is a side sectional view of the implantable shunt according to the example implementation shown in FIG. 2A.

FIGS. 2A and 2B are top and side sectional views of an implantable shunt 200 according to another example implementation of the present invention. The implantable shunt 200 includes a shunt valve 205. Because like numbered components in FIGS. 2A and 2B correspond to similar components shown in the shunt valve 105 of FIGS. 1A and 1B, not all components of the shunt valve 205 will be described herein in detail. The implantable shunt 200 includes a resilient member 208, which can be a spring, and a fluid regulating device 216 connected to the resilient member 208. The fluid regulating device 216 selectively permits fluid flow through the implantable shunt 200 according to an adjustable opening pressure that is proportional to an amount of tension on the resilient member 208. A tension sensor 210 that is attached to the surface of the resilient member 208 is configured as a strain gauge, which may include resistive, capacitive, and/or semiconductor type sensors. The tension sensor 210 measures an amount of tension on the resilient member 208 and generates tension data that corresponds to the measured amount of tension.

Figure 2C:
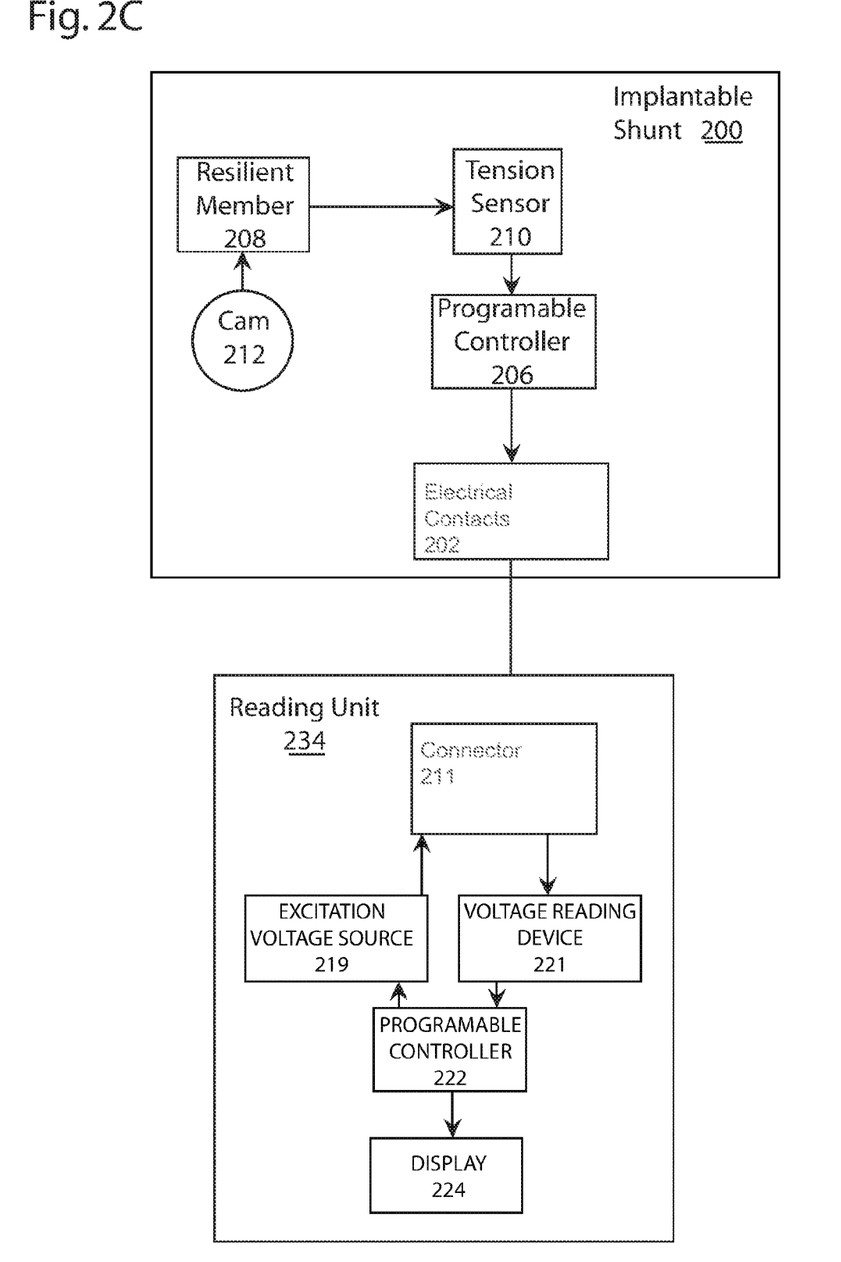
FIG. 2C is a block diagram illustrating an implantable shunt system including an implantable shunt according to the example implementation shown in FIGS. 2A and 2B.

Now also referring to FIG. 2C, the tension data is transmitted from the tension sensor 210 to a reading unit 234 via a connector 211. Electrically conductive needle probes 212a, 212b, 212c of the connector 211 can puncture into a reservoir 214 of the implantable shunt 200 to electrically connect to electrical contacts 202a, 202b, 202c, 202d. The electrical contacts 202a-202d are connected to a programmable controller 206 via wires 204 and/or conductive leads. The implantable shunt 200 can be surgically implanted under the scalp of a patient and configured for hydrocephalus. When fluid pressure at an inlet opening 228 exceeds a predetermined threshold, fluid flows into the chamber 228 of the shunt valve 205 via the inlet opening 218 and through the outlet opening 226. The fluid regulating device 216 is a ball that selectively engages with a valve seat 220. As shown, the resilient member 208 is a spring that biases the ball 216 to the valve seat 220 to selectively allow or prevent fluid flow.

The reading unit 234 includes a voltage reading device 221 that reads voltage of the electrical signal received from the tension sensor 210, which may indicate pressure associated with the fluid regulating device 216. Programmable controllers 206 and 222 may include one or more processors, a memory connected to the one or more processors, and one or more storage devices for storing non-transitory data and instructions that, when executed by the one or more processors, cause the programmable controller 106 to perform specific functions that can include analog-to-digital signal conversion and determining a pressure and/or position of the implanted shunt 200 based on the tension data. The programmable controller 222 can determine the opening pressure of the fluid regulating device 216 and a position of the cam 212 based on the received tension data. The cam 212 is connected to the resilient member 208, and the tension on the resilient member 208 is proportional to the position of the cam 212.

An excitation voltage source 219 of the reading unit 234 can provide power to the implantable shunt 200 in order to activate the tension sensor 210 to transmit the tension data. The reading unit 234 also includes a display 224 that is connected to the programmable controller 222. The display 224 displays one or more visual representations associated with the received tension data, such as plots, graphs, tables, and/or numerical representations of position and/or pressure of the implantable shunt 200 as indicated by the tension data.

As briefly described above and as shown in FIGS. 2A and 2C, a connector 211 includes electrically conductive needle probes (protruding members) 212a, 212b, 212c that are electrically connectable to respective electrical contacts 202a, 202b, 202c in a reservoir 214 of the implantable shunt 200, such that the tension sensor 210 can be electrically connected to the reading unit 234, in order to communicate tension data from the tension sensor 210 and activation command signals from the reading unit 234. As shown in FIGS. 3A, 3B, 4A and 4B, electrical contacts and conductive protruding members according to example implementations of the present invention can have various arrangements.

Figure 3A:
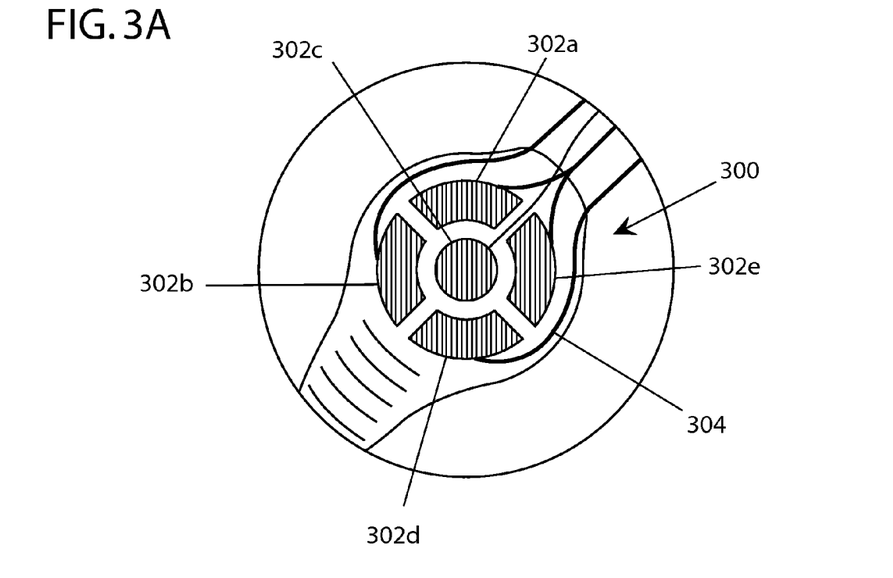
FIG. 3A is top sectional view of electrical contacts in a reservoir of an implantable shunt, according to an example implementation of the present invention.
Figure 3B:
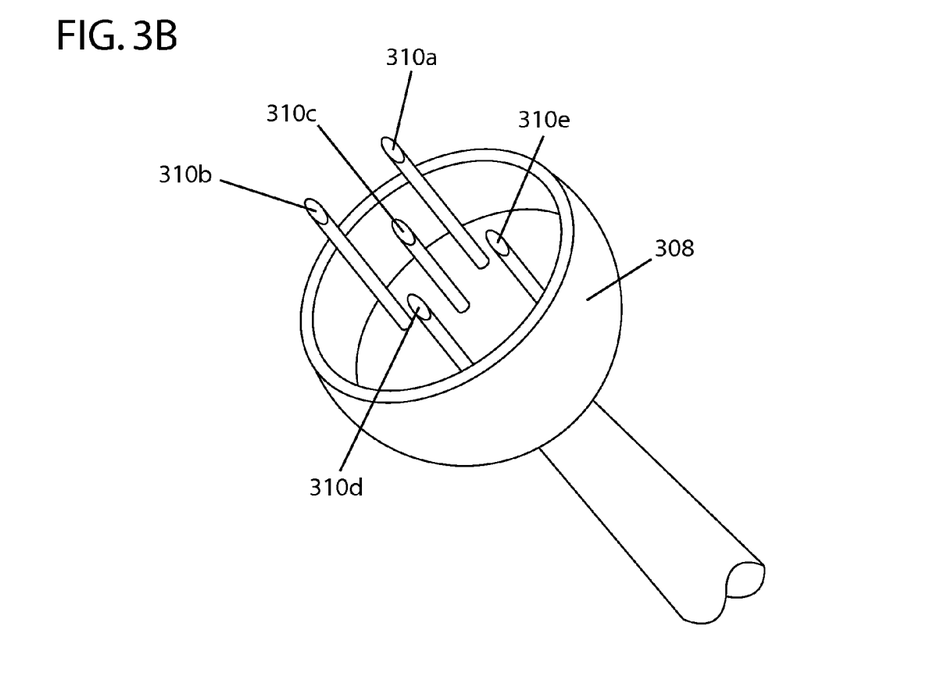
FIG. 3B is a partial view of an electrical connector with electrically conductive protruding members that are connectable to the electrical contacts in the example implementation shown in FIG. 3A.
Figure 4A:
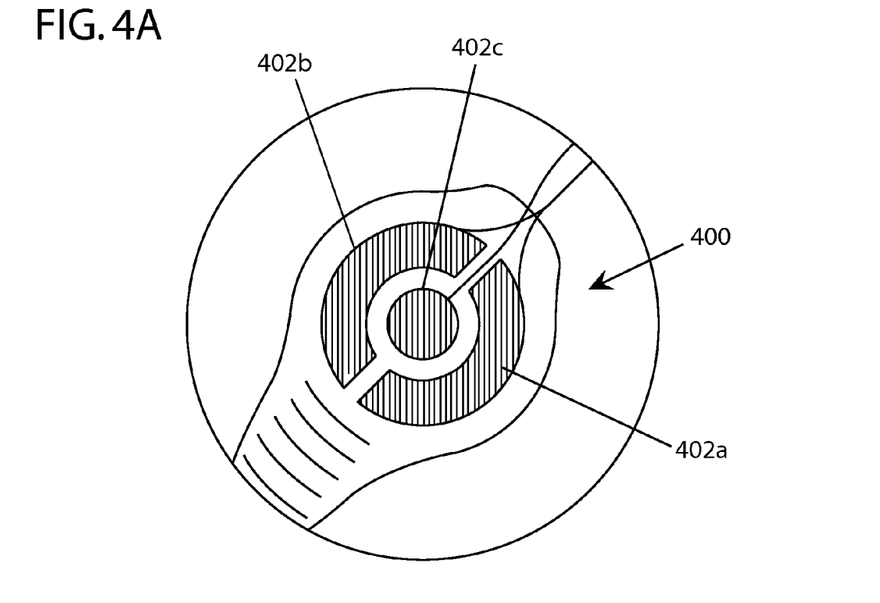
FIG. 4A is a top sectional view of electrical contacts in a reservoir of an implantable shunt, according to another example implementation of the present invention.
Figure 4B:
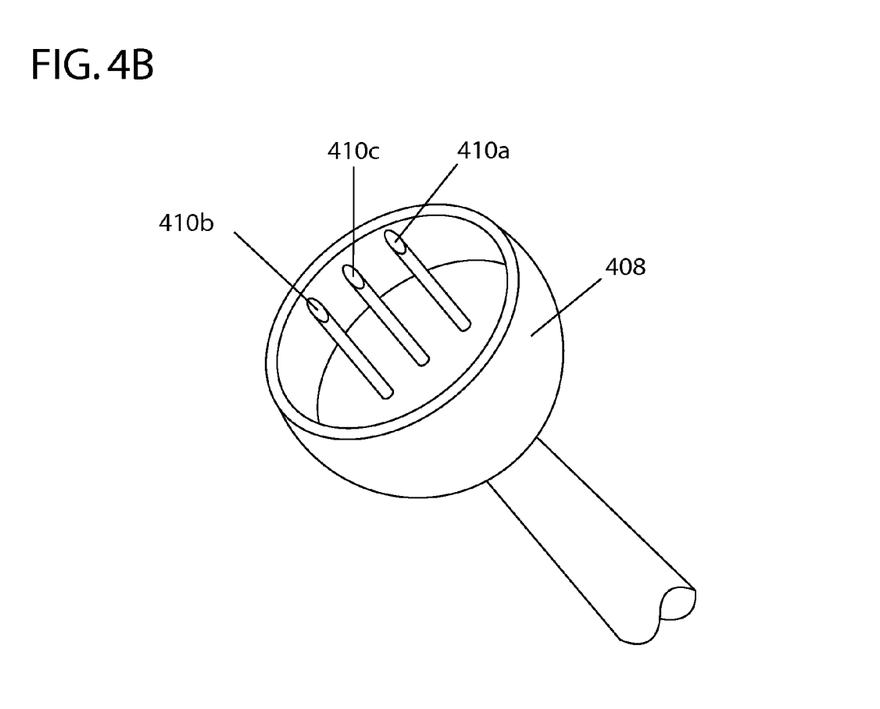
FIG. 4B is a partial view of a connector with electrically conductive protruding members that are connectable to the electrical contacts in the example implementation shown in FIG. 4A.

FIG. 3A is a top sectional view of an arrangement of electrical contacts 302a, 302b, 302c, 302d, and 302e in a reservoir 300 of an implantable shunt. The electrical contacts 302a-302e are electrically connected to respective conductive leads 304. FIG. 3B is a partial view of a connector 308 with electrically conductive needle probes (protruding members) 310a, 310b, 310c, 310d, and 310e that can puncture the skin to enter into the reservoir 300 to connect to respective electrical contacts 302a, 302b, 302c, 302d, 302e shown in FIG. 3A. FIG. 4A is a top sectional view of an arrangement of electrical contacts in which a central contact 402c is disposed between side contacts 402a and 402b, in a reservoir 400 of an implantable shunt. FIG. 4B is a partial view of a connector 408 with electrically conductive needle probes (protruding members) 410a, 410b, and 410c that can puncture the reservoir 400 to connect to respective electrical contacts 402a, 402b, and 402c.

Figure 5:
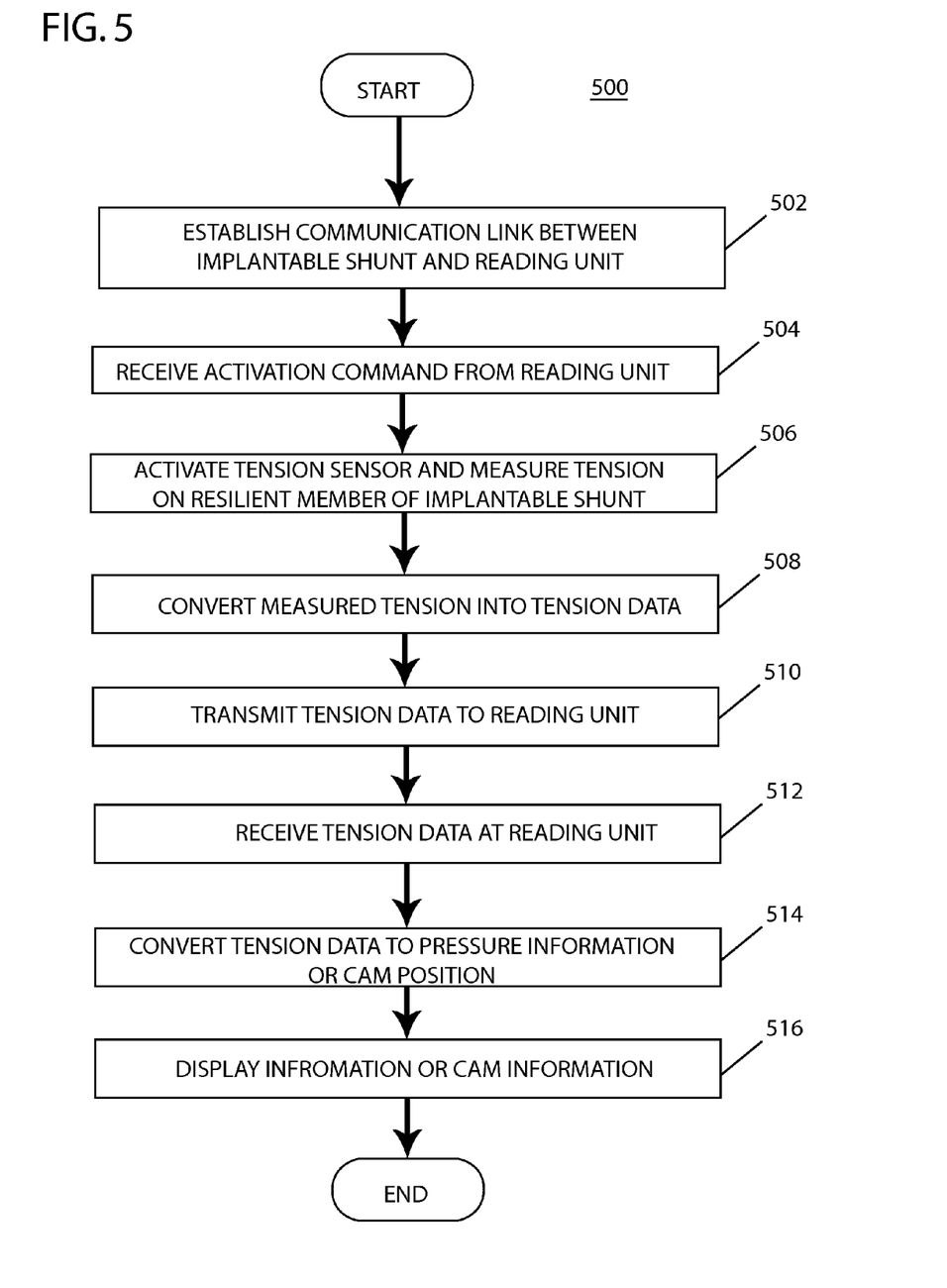
FIG. 5 is a flow diagram illustrating a method of determining pressure and position of an implantable shunt, according to an example implementation of the present invention.

FIG. 5 is a flow diagram illustrating a method 500 of determining position, and thus the opening pressure, of an implantable shunt, according to an example implementation of the present invention. As described above, the reading unit 134, 234 establishes a communication link between itself and the implantable shunt 100, 200 (step 502). This link can be wireless 133 or a direct link between the mating electrical connectors 202, 211. The programmable controller 106, 206 can receive a command to activate the tension sensor 110, 210 (step 504) and take a tension reading of the resilient member 108, 208 (step 506). The tension reading can be converted to tension data (step 508) and transmitted over the communication link to the reading unit 134, 234 (step 510). The reading unit 134, 234 receives the transmitted tension data (step 512) and can convert the tension data to pressure information or cam 112, 212 position (step 514). The pressure information or cam position can then be displayed (step 516).

Note that the conversion of the tension reading to the displayed information can occur either at the shunt controller 106, 206 or the reading unit controller 138, 238 or parts thereof. Thus, the shunt controller 106, 206 can fully process the results generated by the tension sensor 110, 210 and communicate the final information over the communication link.

Alternately, the raw tension reading can be communicated over the communication link and the reading unit controller 138, 238 can create the final information to be displayed.

Numerous characteristics and advantages have been set forth in the foregoing description, together with details of structure and function. While the invention has been disclosed in several forms, it will be apparent to those skilled in the art that many modifications, additions, and deletions, especially in matters of shape, size, and arrangement of parts, can be made therein without departing from the spirit and scope of the present invention and its equivalents as set forth in the following claims. Therefore, other modifications or implementations as may be suggested by the teachings herein are particularly reserved as they fall within the breadth and scope of the claims here appended.

What is claimed is:

1. A method of determining pressure and cam position of an implantable shunt, comprising:
measuring, by a programmable controller, an amount of tension on a resilient member of the implantable shunt, by at least one tension sensor connected to the resilient member that generates tension data corresponding to the measured amount of tension;
transmitting the generated tension data over a communication link, by a transmitting unit;
receiving, by a reading unit the transmitted tension data over the communication link; and
computing both a pressure associated with the implanted shunt and a position of a cam connected to the resilient member, based on the received tension data.

2. The method of claim 1, further comprising electrically connecting, by a connector, the reading unit to the transmitting unit,
wherein connecting the reading unit to the transmitting unit comprises connecting at least one electrically conductive protruding member of the connector to electrical contacts in a reservoir of the implantable shunt.

3. The method of claim 2, wherein the communications link is a wireless communications link and receiving, by the reading unit, the transmitted data over the communication link comprises receiving the tension data over the wireless communications link.

4. The method of claim 3, wherein determining, by the programmable controller, at least one of the pressure or position associated with the implanted shunt based on the received tension data comprises determining an opening pressure of a fluid regulating device connected to the resilient member that selectively permits fluid flow through an opening valve of the implanted shunt, wherein the opening pressure is proportional to an amount of tension on the resilient member.

5. The method of claim 3, further comprising displaying, by a display device connected to the programmable controller, visual representations of at least one of the pressure or position associated with the implanted shunt, based on the received tension data.

6. The method of claim 1, wherein transmitting the tension data over the communication link comprises wirelessly transmitting the tension data over a wireless communication link.

7. The method of claim 6, further comprising receiving, by a wireless antenna, an activation command signal over the wireless communication link.

8. The method of claim 7, further comprising causing, by the programmable controller electrically connected to the wireless antenna, the at least one tension sensor to measure the tension on the resilient member in response to receiving the activation command signal.

9. The method of claim 8, further comprising causing, by the programmable controller, the wireless antenna to transmit the tension data over the wireless communication link in response to receiving the activation command signal.

10. The method of claim 1, wherein measuring the amount of tension on the resilient member by the at least one tension sensor comprises measuring the amount of tension on the resilient member by two or more tension sensors connected to the resilient member at different respective locations.

11. The method of claim 1, wherein the communications link is a wireless communications link and receiving, by the reading unit, the transmitted data over the communication link comprises receiving the tension data over the wireless communications link.

* * * * *